(12) United States Patent
Vouillamoz et al.

(10) Patent No.: US 10,052,435 B2
(45) Date of Patent: Aug. 21, 2018

(54) SKIN-ATTACHABLE MINIATURE DRUG INJECTION DEVICE WITH REMOTE ACTIVATION CAPABILITY AND DRY DRUG CARRIER WITHIN INJECTION NEEDLE

(71) Applicant: Preciflex SA, Neuchâtel (CH)

(72) Inventors: Lucien Vouillamoz, Feusisberg (CH); Melissa Rosen, Salem, MA (US); Judy L. Walish, Brighton, MA (US); Daniel Yasevac, Somerville, MA (US); Michel Bruehwiler, Newton, MA (US)

(73) Assignee: Preciflex SA, Neuchâtel (CH)

( * ) Notice: Subject to any disclaimer, the term of this patent is extended or adjusted under 35 U.S.C. 154(b) by 731 days.

(21) Appl. No.: 14/375,466

(22) PCT Filed: Jan. 30, 2013

(86) PCT No.: PCT/IB2013/000659
§ 371 (c)(1),
(2) Date: Jul. 30, 2014

(87) PCT Pub. No.: WO2013/114221
PCT Pub. Date: Aug. 8, 2013

(65) Prior Publication Data
US 2015/0011976 A1    Jan. 8, 2015

(51) Int. Cl.
*A61M 5/00*    (2006.01)
*A61M 5/172*    (2006.01)
(Continued)

(52) U.S. Cl.
CPC ......... *A61M 5/172* (2013.01); *A61B 17/3496* (2013.01); *A61M 5/1454* (2013.01);
(Continued)

(58) Field of Classification Search
CPC .... A61M 37/0069; A61M 2005/14252; A61M 2005/1585; A61M 2005/206; A61M 2005/2013
See application file for complete search history.

(56) References Cited

U.S. PATENT DOCUMENTS 3,961,622 A    6/1976  Edwards
4,652,261 A *  3/1987  Mech .................. A61D 7/00
                                                    119/859
(Continued)

FOREIGN PATENT DOCUMENTS

FR    1552838    1/1969
FR    2 210 910    7/1974
(Continued)

OTHER PUBLICATIONS

International patent application No. PCT/IB2013/000659, International Search Report, dated Jun. 10, 2014.
(Continued)

*Primary Examiner* — Kevin C Sirmons
*Assistant Examiner* — William Carpenter
(74) *Attorney, Agent, or Firm* — Da Vinci Partners LLC; John Moetteli

(57) ABSTRACT

An active agent or drug injecting device (10) includes a main housing (16) containing a trigger mechanism (24) which can be manually activated via release bar (32) or remotely triggered via wireless receiver (70) activating motor (74), and a second housing (80) containing an injection- and needle-assembly (22). The needle (30) encloses a dry carrier (26) having an active agent (12) disposed thereon. The trigger mechanism triggers the injection assembly to propel the needle into the skin (via spring (54)), to inject the active agent into a living organism (either by letting the active agent diffuse out of the needle or by actively flushing it out),
(Continued)

and to subsequently retract the needle back into the housing (80) (via spring (64)).

17 Claims, 14 Drawing Sheets

(51) Int. Cl.
  *A61M 5/20* (2006.01)
  *A61B 17/34* (2006.01)
  *A61M 5/32* (2006.01)
  *A61M 5/158* (2006.01)
  *A61M 5/142* (2006.01)
  *A61M 5/152* (2006.01)
  *A61M 5/155* (2006.01)
  *A61M 5/315* (2006.01)
  *A61M 5/145* (2006.01)
  *A61M 5/30* (2006.01)
  *A61M 5/31* (2006.01)
  *A61B 17/00* (2006.01)

(52) U.S. Cl.
  CPC ...... *A61M 5/14248* (2013.01); *A61M 5/2033* (2013.01); *A61M 5/2053* (2013.01); *A61M 5/2066* (2013.01); *A61M 5/3234* (2013.01); *A61M 5/3291* (2013.01); *A61M 5/3294* (2013.01); *A61B 2017/00132* (2013.01); *A61B 2017/00212* (2013.01); *A61M 5/152* (2013.01); *A61M 5/155* (2013.01); *A61M 5/31531* (2013.01); *A61M 5/3202* (2013.01); *A61M 5/326* (2013.01); *A61M 5/3273* (2013.01); *A61M 5/3293* (2013.01); *A61M 2005/1426* (2013.01); *A61M 2005/14252* (2013.01); *A61M 2005/14256* (2013.01); *A61M 2005/14268* (2013.01); *A61M 2005/14506* (2013.01); *A61M 2005/1581* (2013.01); *A61M 2005/1583* (2013.01); *A61M 2005/1585* (2013.01); *A61M 2005/206* (2013.01); *A61M 2005/2073* (2013.01); *A61M 2005/2086* (2013.01); *A61M 2005/3022* (2013.01); *A61M 2005/3142* (2013.01); *A61M 2205/3561* (2013.01); *A61M 2205/3569* (2013.01); *A61M 2205/3592* (2013.01); *A61M 2205/8218* (2013.01); *A61M 2205/8293* (2013.01); *A61M 2209/01* (2013.01); *A61M 2209/088* (2013.01); *A61M 2210/12* (2013.01)

(56) References Cited

U.S. PATENT DOCUMENTS

| | | |
|---|---|---|
| 5,562,613 A | 10/1996 | Kaldany |
| 2004/0010207 A1* | 1/2004 | Flaherty .............. A61B 5/157 600/573 |
| 2004/0092874 A1 | 5/2004 | Mazidji et al. |
| 2005/0203461 A1* | 9/2005 | Flaherty ............ A61M 5/14248 604/131 |
| 2006/0211982 A1* | 9/2006 | Prestrelski .......... A61K 9/0014 604/60 |
| 2007/0066938 A1* | 3/2007 | Iio ....................... A61B 5/1411 604/152 |
| 2007/0197968 A1* | 8/2007 | Pongpairochana ..... A61M 5/20 604/131 |
| 2012/0197210 A1* | 8/2012 | Kuhn ................. A61M 5/2448 604/200 |

FOREIGN PATENT DOCUMENTS

| | | |
|---|---|---|
| WO | WO 98/34657 | 8/1998 |
| WO | WO 2004/006982 | 1/2004 |
| WO | WO 2007/051563 | 5/2007 |
| WO | WO 2009/023798 | 2/2009 |
| WO | WO 2010/149734 | 12/2010 |

OTHER PUBLICATIONS

International Search Report, International patent application No. PCT/IB2015/000446, dated Nov. 13, 2015.

* cited by examiner

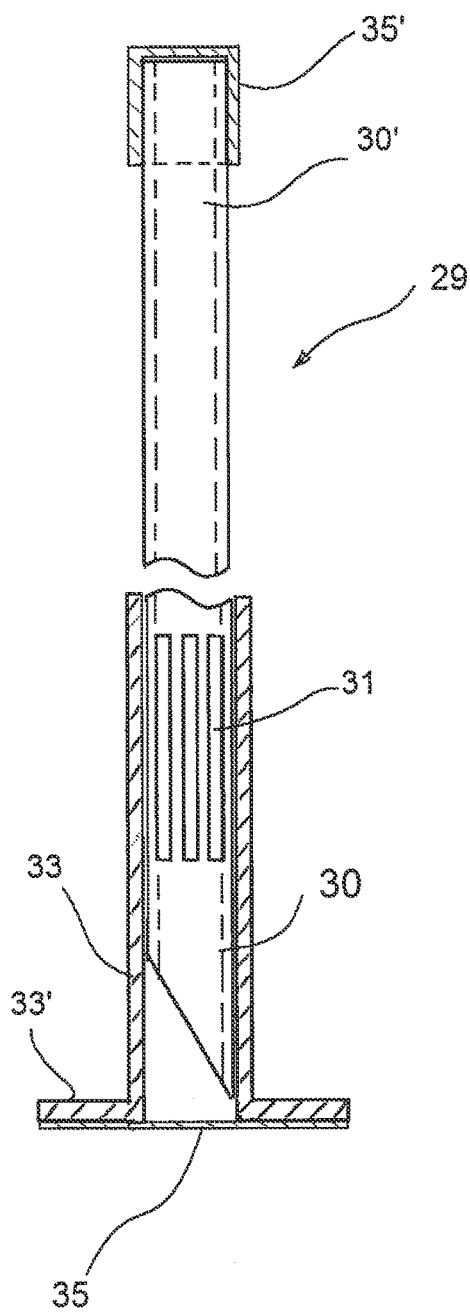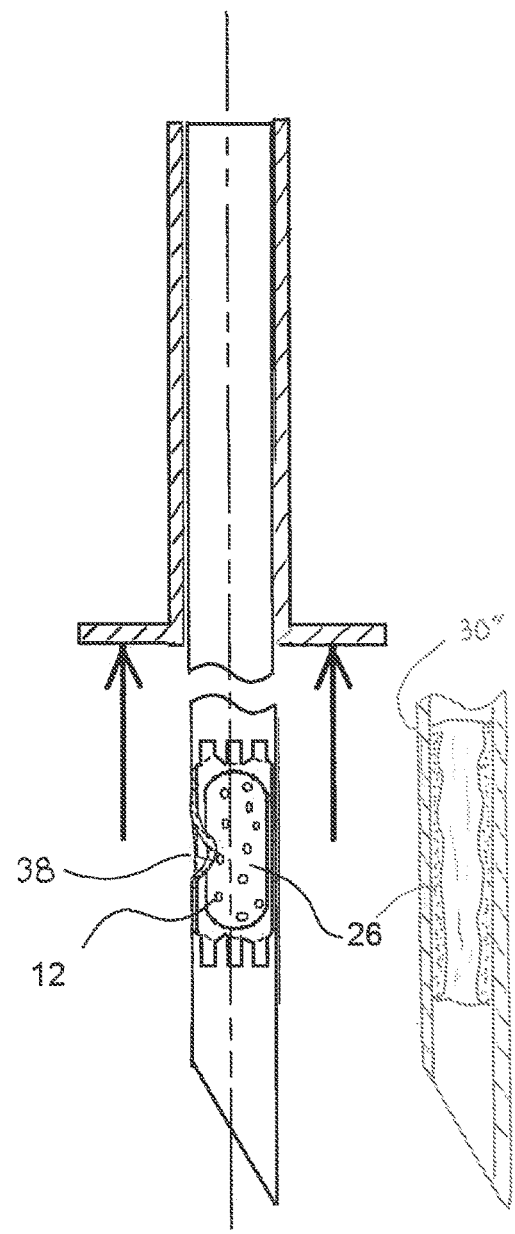
FIG. 3A  FIG. 3B
FIG. 3C

SKIN-ATTACHABLE MINIATURE DRUG INJECTION DEVICE WITH REMOTE ACTIVATION CAPABILITY AND DRY DRUG CARRIER WITHIN INJECTION NEEDLE

CROSS REFERENCE TO RELATED APPLICATIONS

This application is the National Stage of International Application No. PCT/IB2013/000659, filed Jan. 30, 2013, which claims benefit under 35 USC § 119(a), to U.S. provisional patent application Ser. No. 61/592,745, filed Jan. 31, 2012.

COPYRIGHT & LEGAL NOTICE

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever. Further, no reference to third party patents or articles made herein is to be construed as an admission that the present invention is not entitled to antedate such material by virtue of prior invention.

BACKGROUND OF THE INVENTION

This invention relates to injector devices and in particular to injector devices for automatically injecting a defined amount of active agent in a living organism.

Prior devices that are capable of injecting an active agent upon a trigger event are cumbersome and bulky, requiring significant or dedicated space, lack accuracy or are too costly for many users.

What is needed is an active agent injector that provides an automatic injection of an active agent upon a trigger event and yet remains simple and highly compact.

SUMMARY OF THE INVENTION

An active agent injecting device of the invention dispenses a measured amount of active agent into a living organism. The injecting device includes a main housing, an injection assembly and a trigger mechanism. The main housing houses the operative components of the device. A needle encloses a carrier having an active agent disposed thereon. The trigger mechanism triggers the injection assembly to release the needle to inject the active agent into the living organism.

An object of the invention is to provide an active agent injector which takes up minimal space.

Another object of the invention is to provide a compact active agent injector which adapts to requirements which do not readily permit prior art active agent injectors, such as when such injector is worn on a wrist, ankles, a head or around or along some part of human body, or on objects such as clothes and sporting articles.

BRIEF DESCRIPTION OF THE DRAWINGS

FIG. 3A is a partial cross sectioned side view of the needle assembly of the active agent injector of the invention, in the pre-injection position.

FIG. 3B is a partial breakaway, partial cross-sectioned side view of the needle assembly of the active agent injector of the invention, in the post-injection position.

FIG. 3C is a partial breakaway, partial cross-sectioned side view of an alternate needle assembly of the active agent injector of the invention.

Those skilled in the art will appreciate that elements in the figures are illustrated for simplicity and clarity and have not necessarily been drawn to scale. For example, dimensions may be exaggerated relative to other elements to help improve understanding of the invention and its embodiments. Furthermore, when the terms 'first', 'second', and the like are used herein, their use is intended for distinguishing between similar elements and not necessarily for describing a sequential or chronological order. Moreover, relative terms like 'front', 'back', 'top' and 'bottom', and the like in the description and/or in the claims are not necessarily used for describing exclusive relative position. Those skilled in the art will therefore understand that such terms may be interchangeable with other terms, and that the embodiments described herein are capable of operating in other orientations than those explicitly illustrated or otherwise described.

DETAILED DESCRIPTION OF THE PREFERRED EMBODIMENT(S)

The following description is not intended to limit the scope of the invention in any way as they are exemplary in nature and serve to describe the best mode of the invention known to the inventors as of the filing date hereof. Consequently, changes may be made in the arrangement and/or function of any of the elements described in the disclosed exemplary embodiments without departing from the spirit and scope of the invention.

Figure 1:
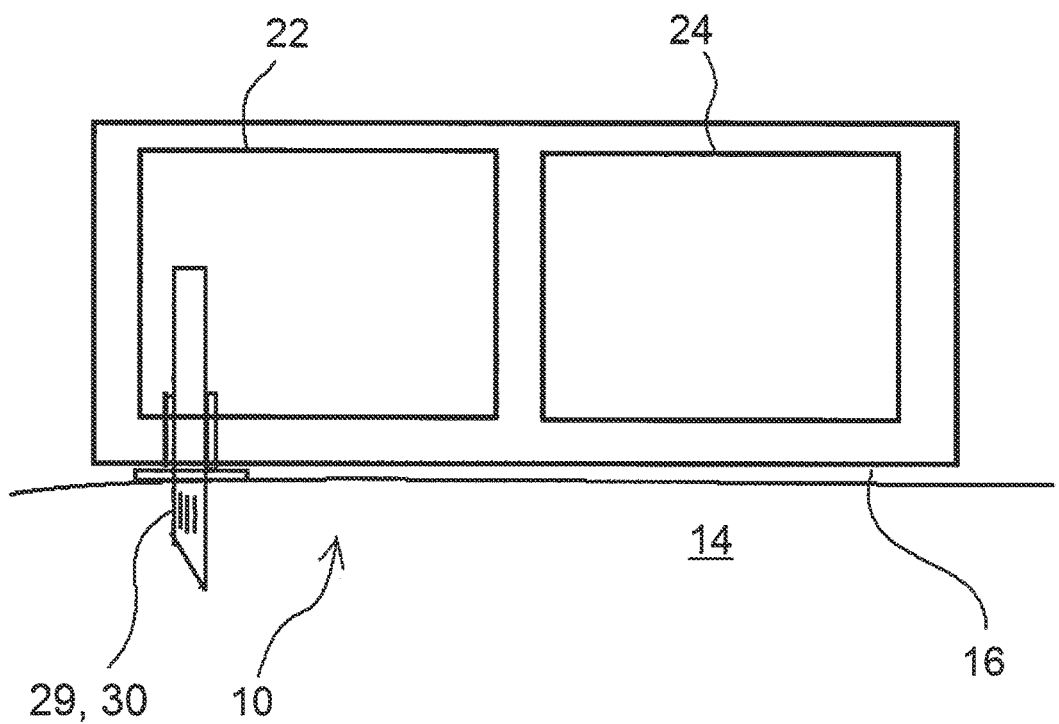
FIG. 1 is a schematic representation of the active agent injector of the invention.

Referring now to FIG. 1, in schematic view, the active agent injector 10 includes a trigger mechanism 24, and an injector assembly 22 enclosed in a housing 16.

Figure 2:
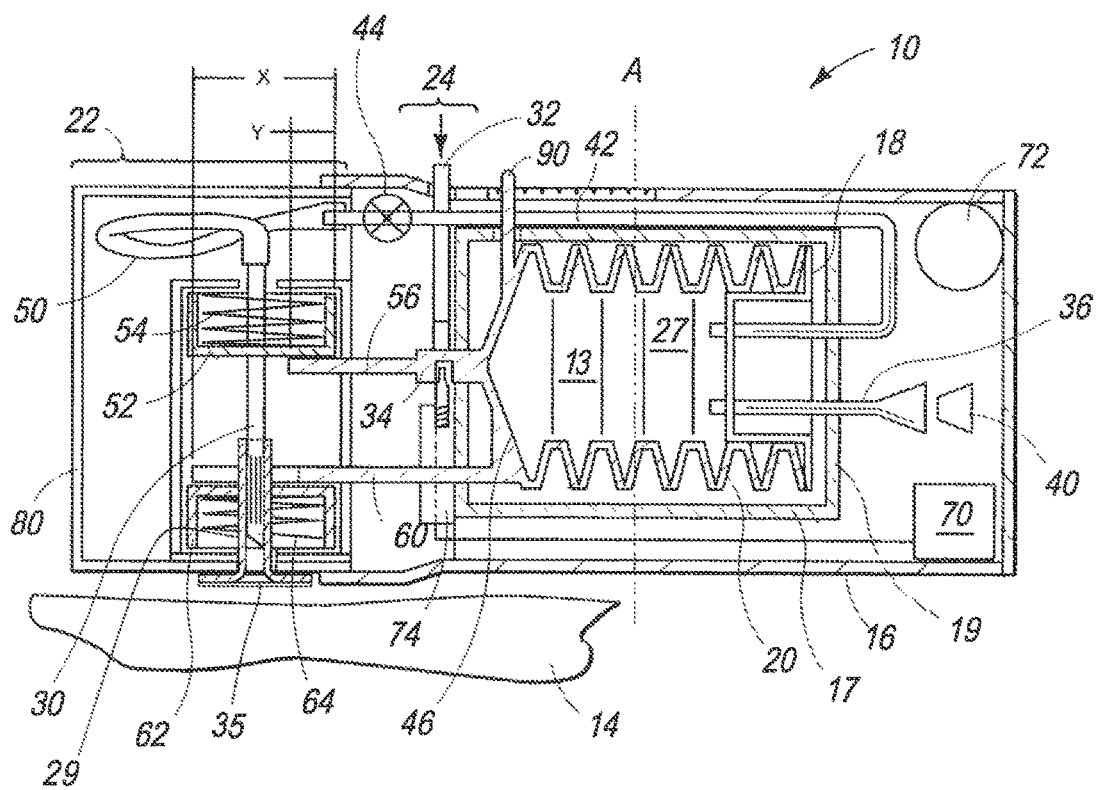
FIG. 2 is a cross sectional side view of the active agent injector of the invention.
Figure 4:
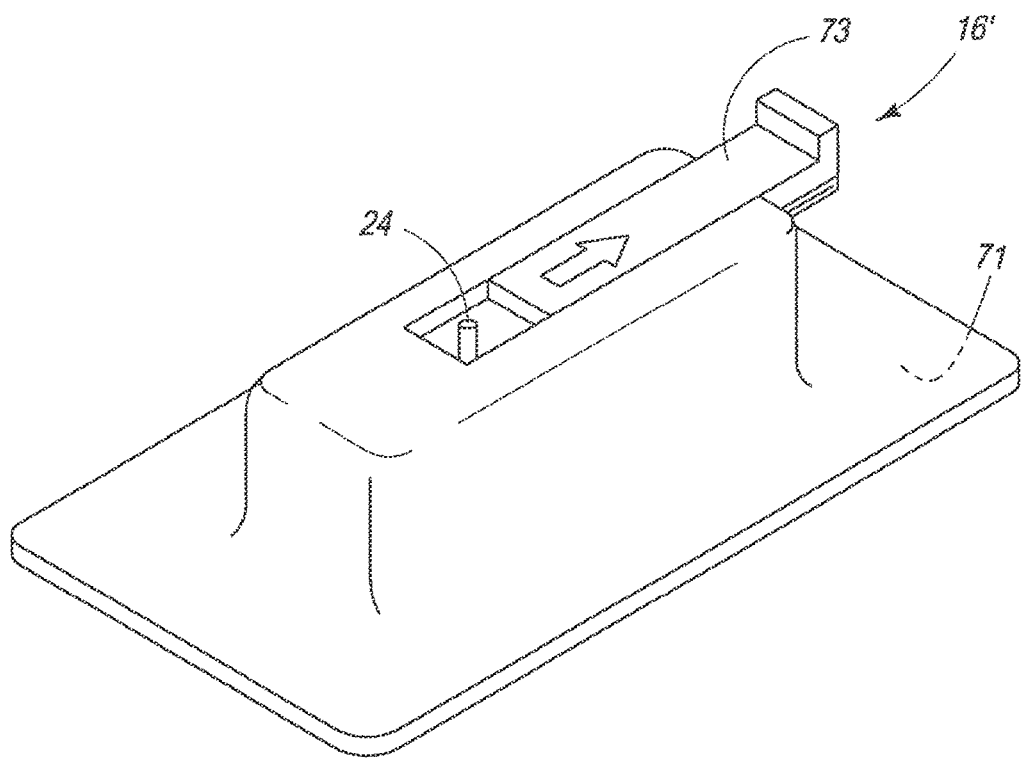
FIG. 4 is a perspective view of an enclosure for the active agent injector of the invention.

Referring now to FIG. 2, an active agent injecting device 10 is adapted to inject an active agent 12 (see FIG. 3B) into a living organism 14. The injecting device 10 includes a main housing 16, an injection assembly 22 and a trigger mechanism 24. The main housing 16 houses the operative components of the device 10. To prepare for operation, the device 10 must be charged with a needle assembly 29 having a dry carrier 26 (such as freeze dried or lyophilized drugs) which, if not itself an active agent 12, comprises active agents for injecting into the living organism 14.

Figure 6:
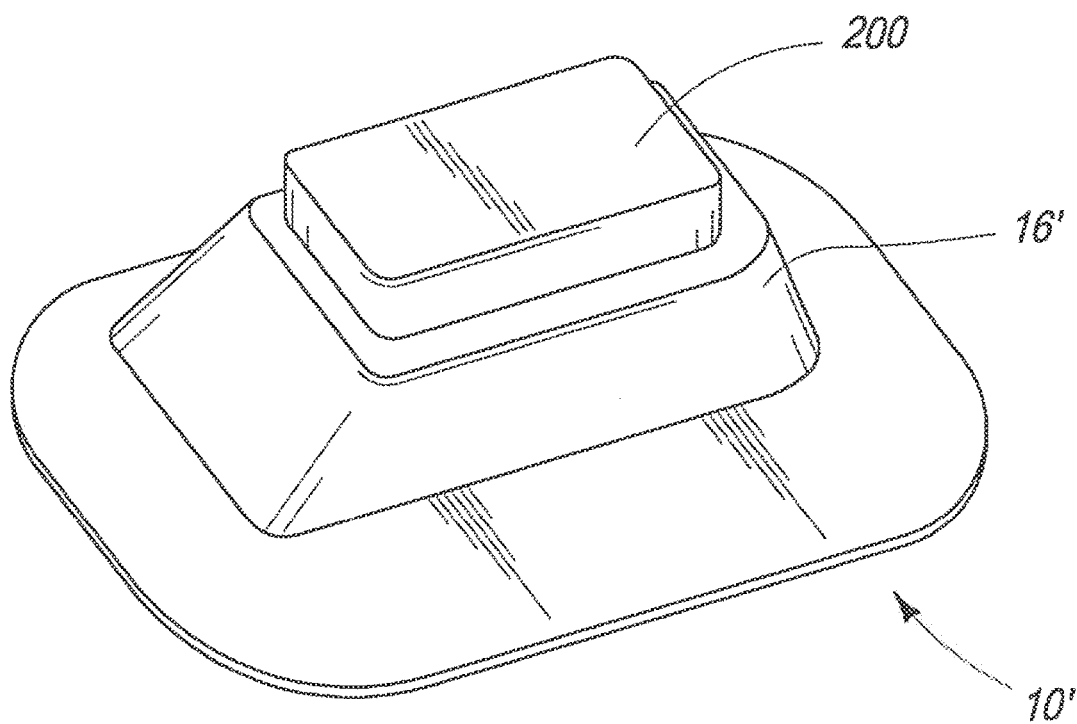
FIG. 6 is a perspective view of an alternate embodiment of the invention, with a modular, remote triggering device of the invention.

FIGS. 3A and 3B are side views of the needle assembly 29 of the active agent injector 10 of the invention, in a pre-injected and an injected position, respectively.

The needle assembly 29 hermetically seals a needle 30 having perforations 31 along the circumference thereof, the perforations being adjacent the dry carrier 26. The needle assembly 29 encloses the dry carrier 26, which, by way of example, can comprise "human serum albumin" (HSA). HSA is advantageous because it is an abundantly occurring protein which presents no problems of immunogenicity (antibodies, allergic reactions, anaphylactic shock, etc.). It is also highly suitable for binding to small molecules, including the active agents 12 (e.g., medicines, drugs, anti-viruses, vitamins, anti-venoms, serums and medications) which are to be injected into the subject organism. Exemplary dry agents or dry carriers for use in the injector of the invention include but are not limited to:

1. SA (serum albumin)
2. nanoparticles
3. liposome formulations (stealth, targeted, cationic, conventional)
4. PEG conjugation
5. any combinations of any 2,3 and/or 4
6. lipoproteins
7. stabilized nanoparticles (ie with polysorbates)
8. carbohydrate carriers The needle 30 is at least partially hollow. In the distal end 30', the needle 30 may be solid in order to facilitate gripping and charging (particularly in a multi-needle system having a magazine of several needle assemblies containing various active agents, not shown) of the needle. A protective sleeve 33 having a flange 33' protects the dry carrier 26 and therefore also the active agent 12 from contamination. The sleeve 33 is sized to form a close sliding fit and/or is sealed using a wax or other sealant which is nontoxic and has a low shear strength. The dry carrier 26 is affixed within the needle 30 via a construct such as an indentation 38 in the side of the needle. Septum membranes 35 and 35' enclose the ends of the needle assembly 29 to hermetically seal such assembly until the time of use. Such membranes 35, 35' may be made from any thin preferably elastic and easily sheared material which is non-toxic and impermeable. Perforations 31 in the needle 30 extend along the needle surface adjacent the dry carrier 26. The perforations 31 allow blood to penetrate and release the active agents 12 in the blood stream of the patient once the flange 33' of the protective sleeve 33, through contact with the skin, is pushed back over the needle 30 thus exposing the perforations 31.

Referring now to FIG. 3C, in an alternate embodiment, the dry carrier/active agent 12, 26 is coated on the inside of the needle 30" and, in subsequent embodiments, is dissolved by the fluid (e.g., saline solution) held in the reservoir 12.

Referring again to FIG. 2, the trigger mechanism 24 triggers the injection assembly 22 to release the needle 30 to insert itself subcutaneously into the living organism 14. The trigger mechanism 24 includes a release bar 32, which when depressed, releases a rod-plunger 34 biased by spring 20 (in this case, the outer surface of the reservoir 13 (which may be empty as no fluid need be used, in which case the distal end of the needle may be closed) which is elastic and so functions as a spring. The release bar 32 (shown also in FIG. 4 as bar 10, in various views) is placed so as to lock in position the left most side 46 of the rod-plunger 34, biased by the spring 20.

The needle 30' in this embodiment includes a cup shaped flange 52 which is integral therewith, which encloses a first extension spring 54. In a set position as shown in the figure, a first motion inhibitor bar 56 extends from the rod-plunger 34 so as to block the motion of the needle 30 against downward motion when the plunger 34 is in its left-most position until the motion inhibitor bar 56 moves far enough to the right to allow the flange 52 to release (and move downward) to eject the needle 30 into the living organism 14. A second motion inhibitor bar 60 blocks a second cup shaped flange 62 which retains a second extension spring 64. Because the spring 20 has a characteristic braking action (caused for example, by the constriction of flow of the fluid therein) that limits the speed of movement when released, a few seconds are required before it reaches its fully expanded position. Note that when the reservoir 13 is a bellows having small air inlets, this may also limit the speed of expansion. Alternatively, a sponge having a small pore size disposed within the bellows, may also be used in place of the spring 20, or act in conjunction therewith, to adjust the speed of movement of the plunger 34 so as to allow enough time for the patient's blood to release the active agent 12 from the dry carrier 26. When enough time has passed to allow release of the active agent 12 into the living organism such that the plunger 34 which is biased by the spring 20 moves sufficiently to the right to pull the second motion inhibiting bar 60 to free the second flange 62, the second flange 62 abuts the first flange 52 and forces the needle 30 out of the living organism 14. The operation cycle of the device 10 is therefore complete, it having inserted the active agent 12 into the living organism 14, followed by automatic retraction of the needle.

The trigger mechanism 24 is controlled by a sensor, a receiver 70, or according to a prescribed dosage, as a function of time. The sensor or receiver 70 may be powered by a power source, such as a battery 72 and control a micromotor 74 which actuates the actuation bar 32. In this manner, triggering need not be manually initiated.

Optionally, the device 10 further includes a second housing 80 for housing the trigger mechanism 22. The second housing 80 releasably connects to the main housing 16 and may be separately disposable from the main housing and its contents.

In an alternate embodiment, the power supply 22 can be solar cells, a wound watch spring, movement captured by an oscillating mass (such as used in automatic watches), or a pneumatic system storing compressed air.

In an alternate embodiment, the device 10 is held against the skin of the living organism 14 by a band (see FIG. 7E) such as a watch band.

The micro injector 10 subcutaneously (>5 mm) injects an active agent 12 within a time frame of 0.5 to 2 sec. A suitable needle size is between 0.3 to 0.45 mm. Preferably, the overall size of the packaging 16' shown in FIG. 4 is about 4 mm in width and about 15 mm in length. The packaging 16' is fixed by gluing on or adhering to the skin with autoadhesive sticker portion 71. The packaging 16' is comprised of a housing 16' and a closure 73 such as a sliding panel to prevent access to the trigger 24 until an active agent 12 is to be dispensed. Optionally, a septum 35, 35", 35'" of a thin, elastic material (on the underside of the device between the needle 30 and the skin 14 of the user) seals the needle injector mechanism 22 from external elements. Note that the sliding panel 73 can be replaced by a remote trigger such as an RF trigger or timed trigger device shown in FIG. 6. A further security device (not shown) which prevents against accidental triggering may be added to improve safety or which is resistant to vibration or shock or material creep.

Figure 5A:
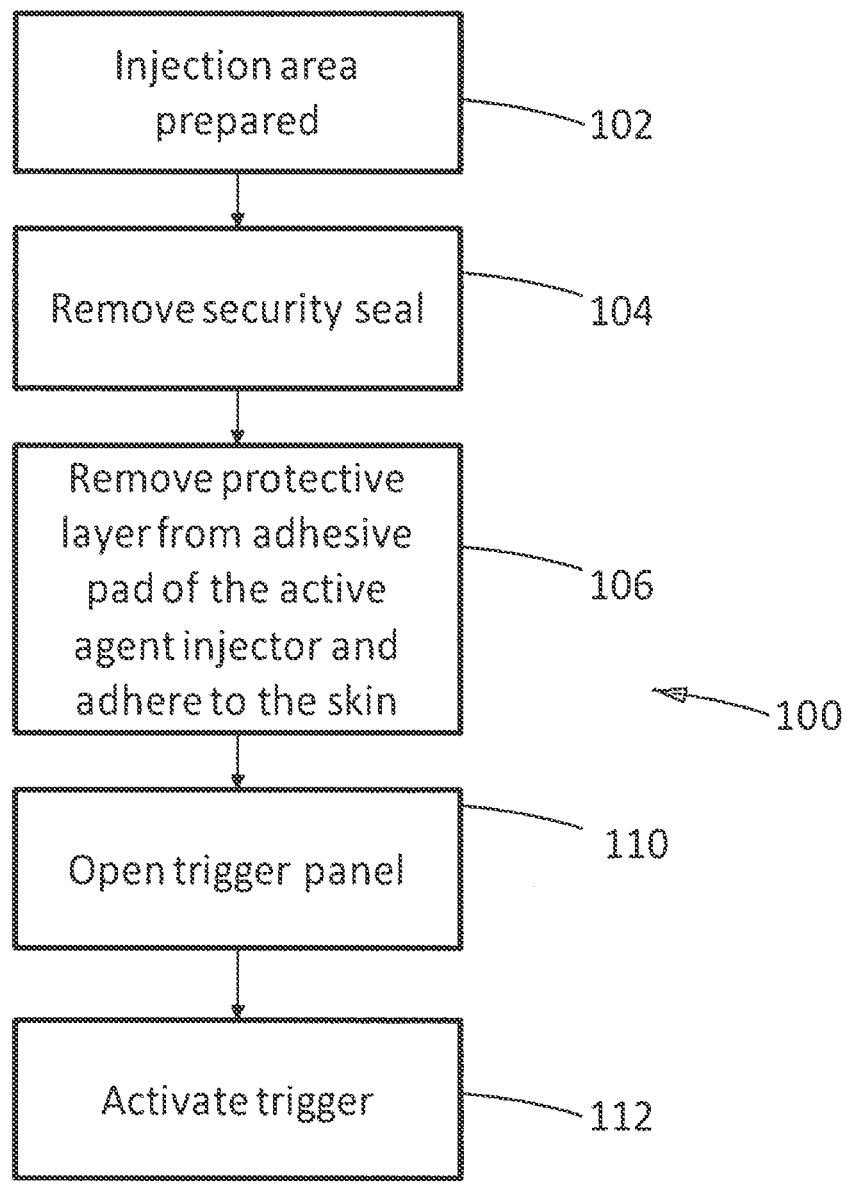
FIG. 5A is a flow chart of an initialization method of the invention, performed by a user or medical professional.

Referring to FIG. 5A, a method 100 of using the invention includes several steps. In a first step 102, the injection area is prepared, for example, cleaning with a disinfectant and a cotton swab. In a second step 104, a security seal on the active agent injector 10 is removed by the user. In a third step 106, a protective layer is removed from an adhesive pad of the active agent injector and the active agent injector is adhered to the skin of the user. In a fourth step 110, the trigger panel is opened by the user to allow access to the trigger. In a fifth step 112, the trigger is activated by the user, thereby initiating the automated process of active agent injection.

Figure 5B:
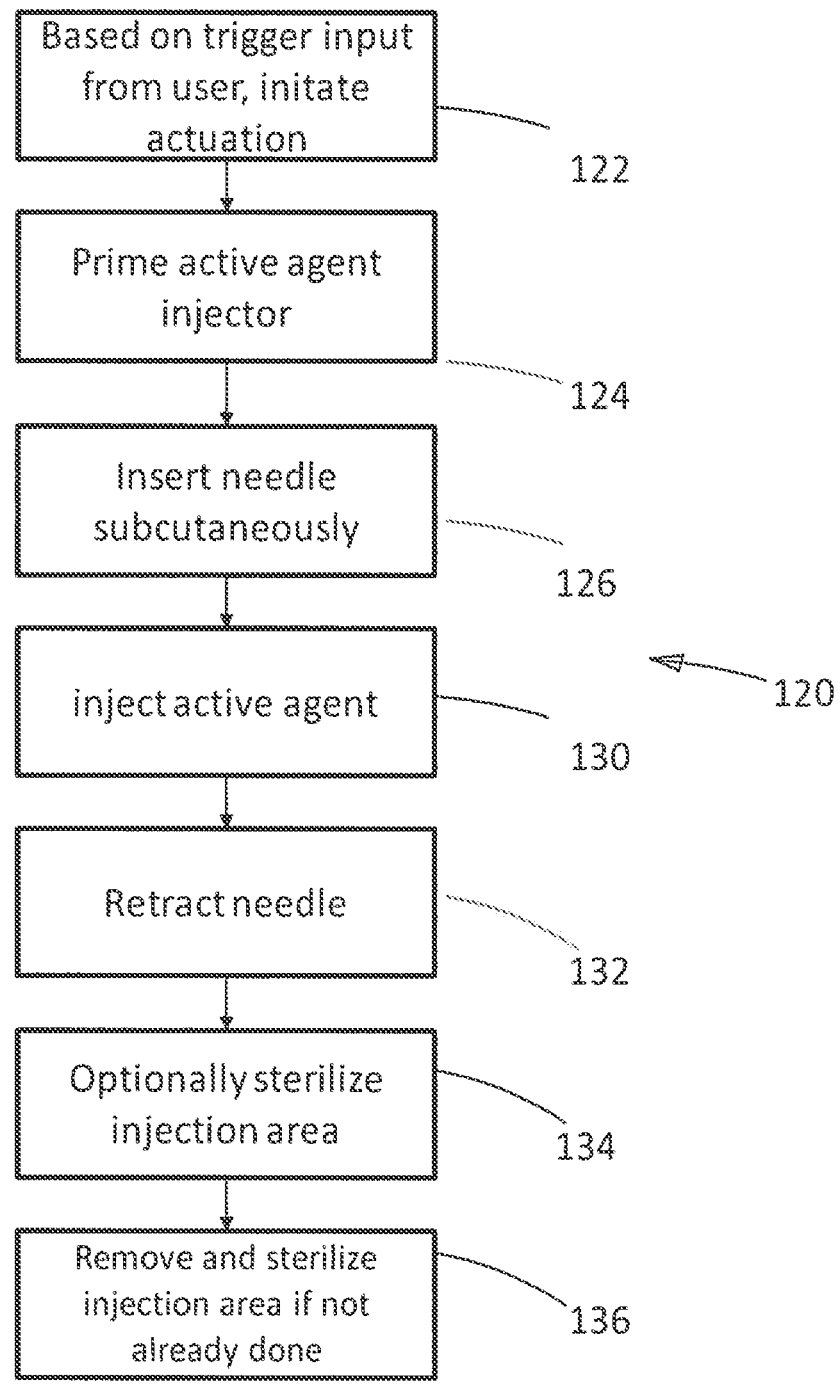
FIG. 5B is a flow chart of a method of the invention executed by the active agent injector.

Referring to FIG. 5B, the automated process 120 of active agent injection is executed by control electronics in the active agent injector 10 and includes several steps. In a first automated step 122, the actuation system of the invention is initiated. In a second automated step 124, the active agent injector 10 is primed. In a third automated step 126, the needle is inserted subcutaneously. In a fourth automated step 130, the active agent 12 is released. In a fifth automated step 132, the needle 30 is retracted. In a sixth automated step 134, optionally, the injection area is sterilized. In a sixth step 136, after use, the active agent injector 10 may be removed by the user and the injection area sterilized, if this has not already been performed.

Referring to FIG. 6, the trigger mechanism 16' of the active agent injector 10' can be controlled via wireless interface in a control module 200 that may be clipped on to the active agent injector 10 so as to interface with the trigger in a manner which can actuate the trigger.

Referring in particular to FIGS. 7A to 7F, a fluid dispensing device 310 of an alternate embodiment carries a solvent (a saline solution for example) in the reservoir 362. The needle 30' of the needle assembly 312 is hollow and provides a channel permitting the solution 27 from entering and flushing the dry carrier 26 into the living organism 14. Upon activation, the device 310 injects the needle 30' under the skin 14 of a patient and the saline solution is dispensed. The solution helps dissolve the dry carrier 26 and so release the drug in the blood. The dry active agent 12 may simply be coated on the inner diameter of the needle 30', so that it can readily react with the incoming solution.

This embodiment has a needle assembly 312 having a first end 314 and a second end 316, preferably beveled to facilitate piercing of the skin of the living organism. The needle assembly 312 is adapted for interfacing, on the first end 314, with a septum 360 in a wall 320 of a flexible hollow membrane 322, and at the second end 316 thereof, for subcutaneously inserting into a living organism 14. The needle assembly 312, about its second end 316, is guided by a guide 324 to permit an injection into the living organism 14 at a substantially non-orthogonal angle alpha with respect to a surface 326 of the living organism. An injection mechanism 330 within a housing 332 includes a hollow transfer collet 334 having a flange 336 at one end thereof and arranged to be translatable lengthwise therein, a compression spring 338 (shown in the compressed state) into which the collet 334 is disposed, the compression spring 338 bearing against the flange 336 at one end thereof and against the housing 332 at the other end thereof, a flexible membrane receiver 340 which is disposed within the transfer collet 334, the flexible membrane receiver 340 having a the needle assembly 312 affixed therein such that the first end 314 is held adjacent the flexible membrane 322 (preferably having a 20 μl capacity) when installed in the receiver 340 and such that the second end 316 is received into the guide 324, and a user push button 342 which abuts one end of the collet 334 and extends outside the housing 332 so as to be accessible by a user. The flexible membrane receiver 340 is connected to a first end 341 of an extension spring 346 having a lesser spring constant K as compared to the extension spring 338, the spring 346 being connected at an opposite end 350 to the housing 332. The flexible membrane receiver 340 having a flange 352 at one end thereof that extends beyond an end face 354 of the flange 336 of the collet holder 334. In the view shown in FIG. 7A, the extension spring 346 is in an essentially relaxed state and the compression spring 338 is in a stressed state. A retaining shoulder 356 on a tang in the housing 332 maintains the compression spring 338 in the stressed state.

Figure 7A:
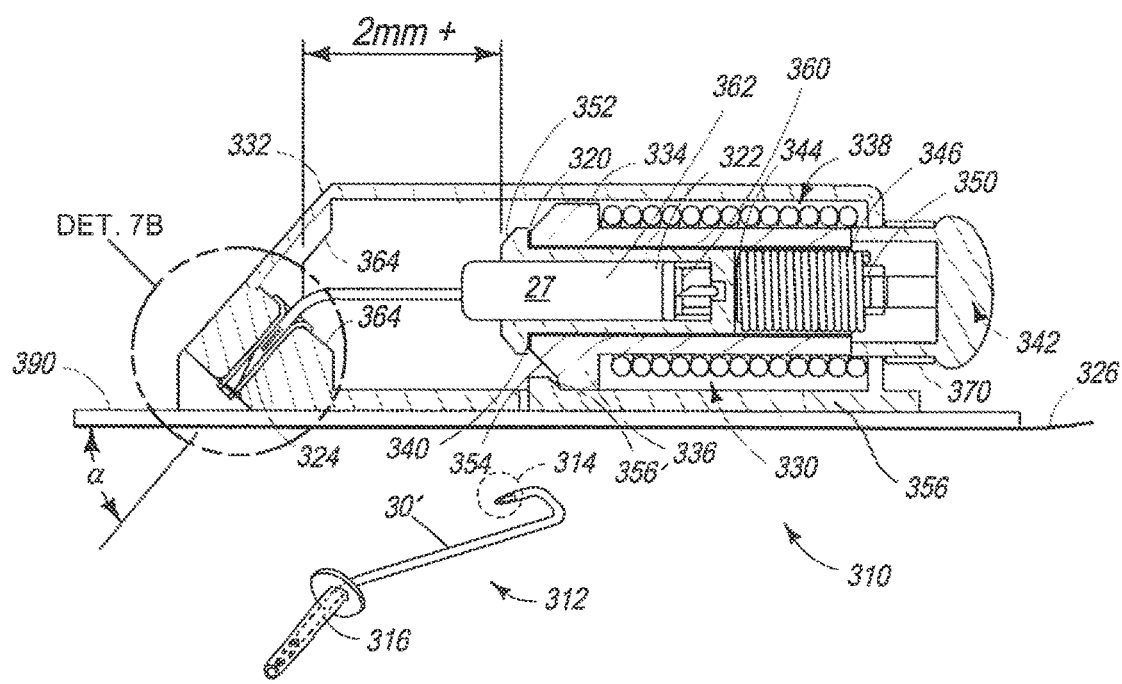
FIG. 7A is a cross-sectional view of a further alternate embodiment of the invention.
Figure 7B:
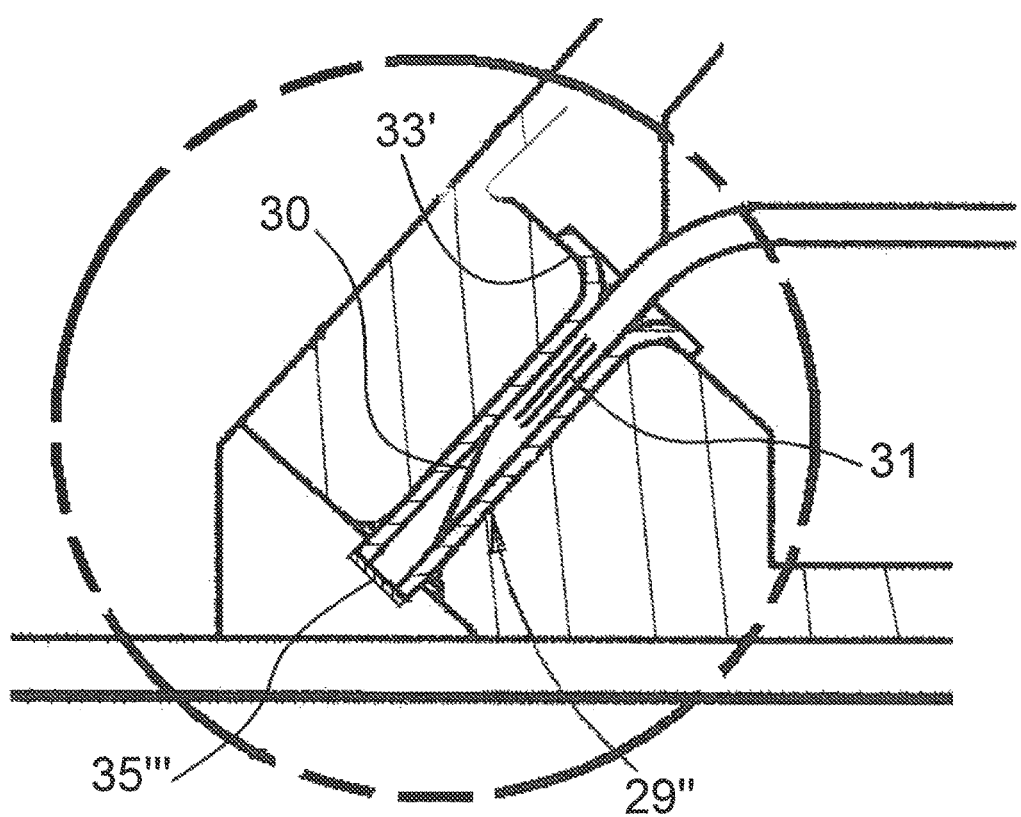
FIG. 7B is a detail view of a portion of the view of the embodiment of FIG. 7A.
Figure 7C:
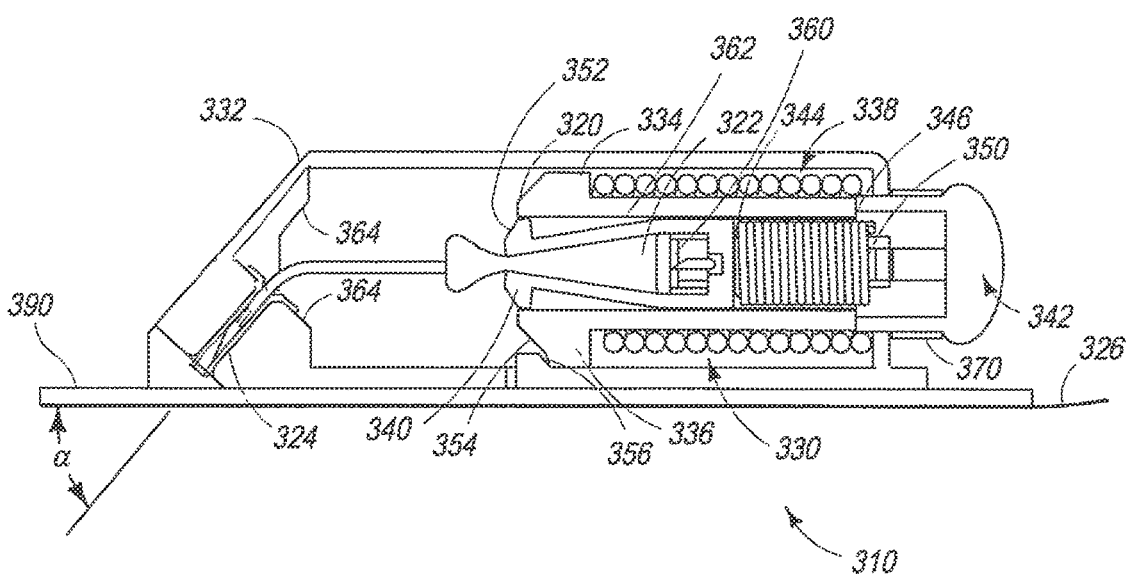
FIGS. 7C and 7D are progressive, partial cross section views of the alternate embodiment of FIG. 7A, showing the progress of the needle during an injection cycle.
Figure 7D:
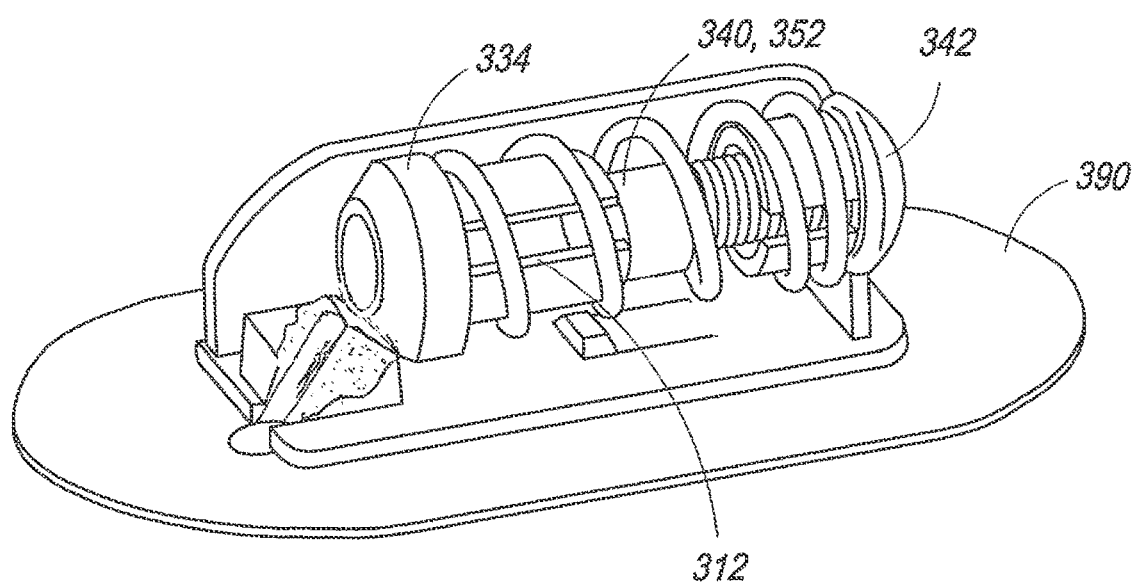

Referring now to FIG. 7B, a detail of the alternate embodiment of FIG. 7A, the needle assembly 29'' includes a sleeve 33 that encloses the needle 30. Slits 31 in the needle 30 are disposed adjacent the dry carrier 26. A membrane 35''' helps ensure a hermetic seal of the needle assembly 29'', preventing contaminants from entering therein.

In operation, a user pushes the button 342 which reacts via the chamfered surface of the collet holder 334 against a flexible cantilever arm 356 to bias the collet over the retaining shoulder 356' thereof, thus allowing the compression spring 338 to expand, thereby translating the flexible reservoir 322 in the receiver 340 along with the needle assembly 312 to an opposite end of the housing 322. During this translation, the first end 314 of the needle assembly 312 penetrates a septum 360 of the fluid reservoir 322 and is primed with the fluid 362 (e.g., the saline solution) contained therein as the needle assembly 312 is guided by the guide 324 toward the surface 326 of the living organism. Further translation, optionally, after priming, then plunges the needle assembly 312 into the living organism 14 a prescribed depth, usually 3 to 5 mm. The receiver flange 352 is sloped so that when it reaches a matched slope or cam surface 364 formed on an inner surface of the housing 332, the receiver 340, which is slotted, collapses (see FIG. 7D) to further squeeze the fluid 362 out of the reservoir 322, expelling the remaining amount of such fluid. In this way, the squeezing is performed laterally with respect to an axis along which the trigger mechanism is actuated. As the receiver flange 352 collapses such that its width is less than the inner diameter of the collet holder 334, the receiver 340 is able to pass through the collet holder 334, drawn therethrough by the extension spring 338 and thus simultaneously drawing the needle assembly 312 out of the living organism 14 safely into the housing 322. Note that here, aspiration of fluids from the body of the living organism 14 is prevented due to the fact that pressure is maintained on the membrane by the tangs of the receiver 340 being held in a collapsed position by the inner surface of the collet 334. At this point, the fluid dispensing device 310 may be removed from the surface 326 of the living organism 14 and be discarded.

As a security against inadvertent activation, a locking construct 370 (similar to the widely known round and ring shaped disposable security seal on the mouth of a plastic milk jug) prevents the push buttons 342 from being depressed.

It should be noted that the solution 27 contained in the reservoir 13 may be any solution which, together with the dry carrier 26, cooperates (even chemically or molecularly reacts or interacts therewith) to inject the desired drug combination in the living organism 14.

Figure 7E:
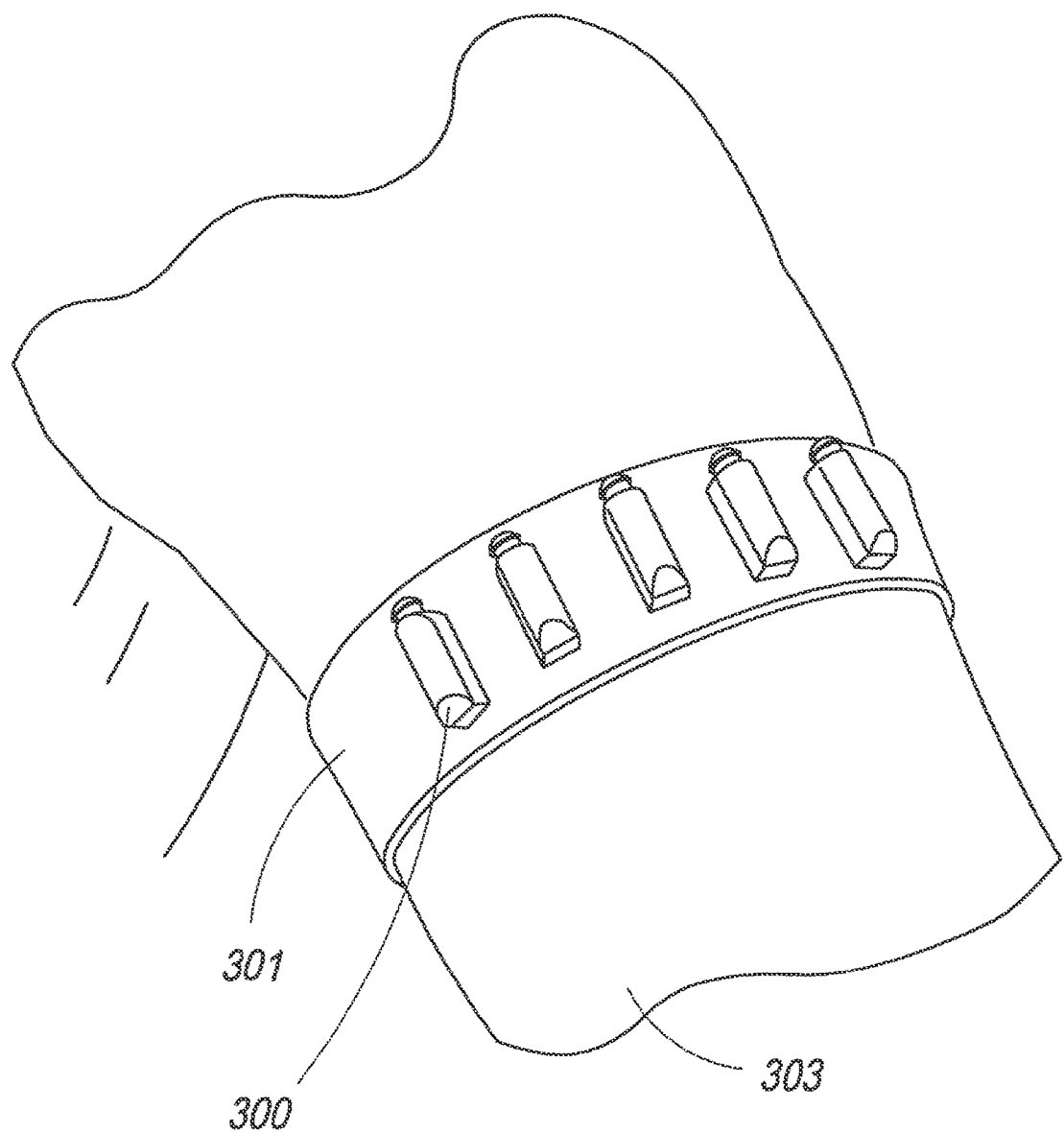
FIG. 7E is a perspective view of a holder of an alternate embodiment of FIG. 7A.

Referring now to FIG. 7E, the fluid dispensing device 300 is retained (via the user holding it against the skin using hand pressure, or via an elastic band 301 (e.g. a watch band or an adhesive or adhesive pad) against the skin of the living organism 14 and may be manually, automatically or remotely actuated to inject a fluid 27 into the living organism 14. For example, the user may simply hold the device 300 against the skin of the living organism 14 to be treated. Alternatively, the elastic band 301 on which the dispensing device 300 (or a series thereof as shown) is affixed may be extended and fastened around an appendage 303 of the living organism 14 so that the base of the housing 332 through which the needle assembly 312 passes is held securely against the skin. For example, the device 300 may be contained in a watch casing mounted on a watch bracelet, such as shown in PCT Application No. PCT/IB2010/002055 and PCT/IB2010/002054, the contents of which are incorporated herein by reference thereto. Optionally, according to the tastes of the wearer, the bracelet 301 and casing may be decoratively formed and/or made of precious metals. Still further, the housing 332 may include a base having a surface on which an adhesive may be applied prior to affixing the device against the skin of the living organism. A self-adhesive pad 390 may also be used.

Figure 7F:
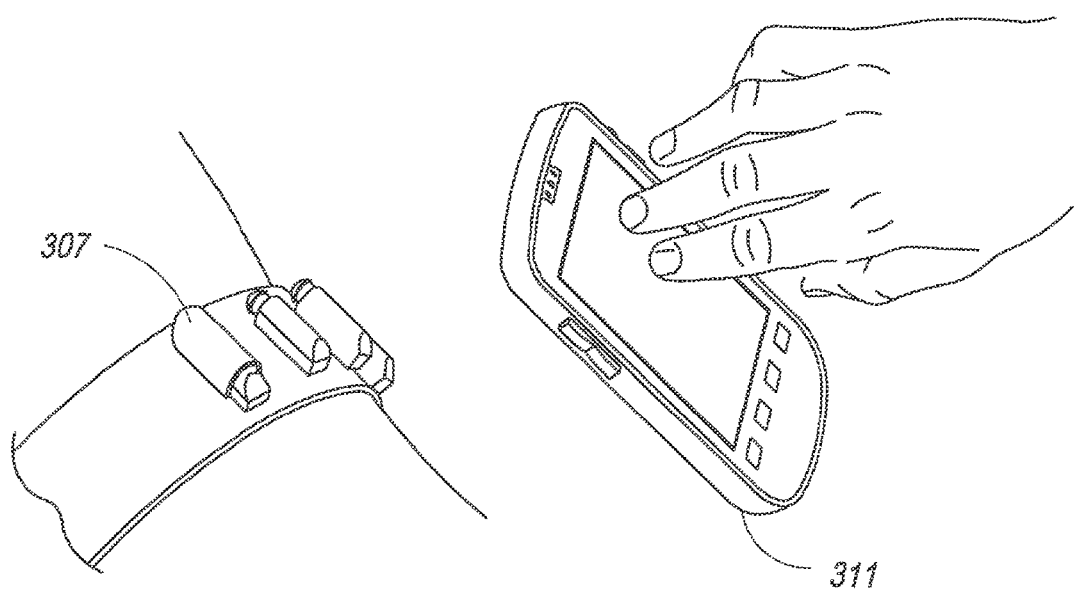
FIG. 7F is a perspective view of a remote actuation device for use with the invention.

Referring now to FIG. 7F, the device 300 may include an attachment 307 into which the device 300 may be placed, the attachment 307 including a radio receiver or the like and an actuator, which receives command signals from a mobile device 311 to actuate the actuator at given times, to automatically administer a dose of fluid 27 and/or dry agent 12 combination to the living organism 14.

Figure 7G:
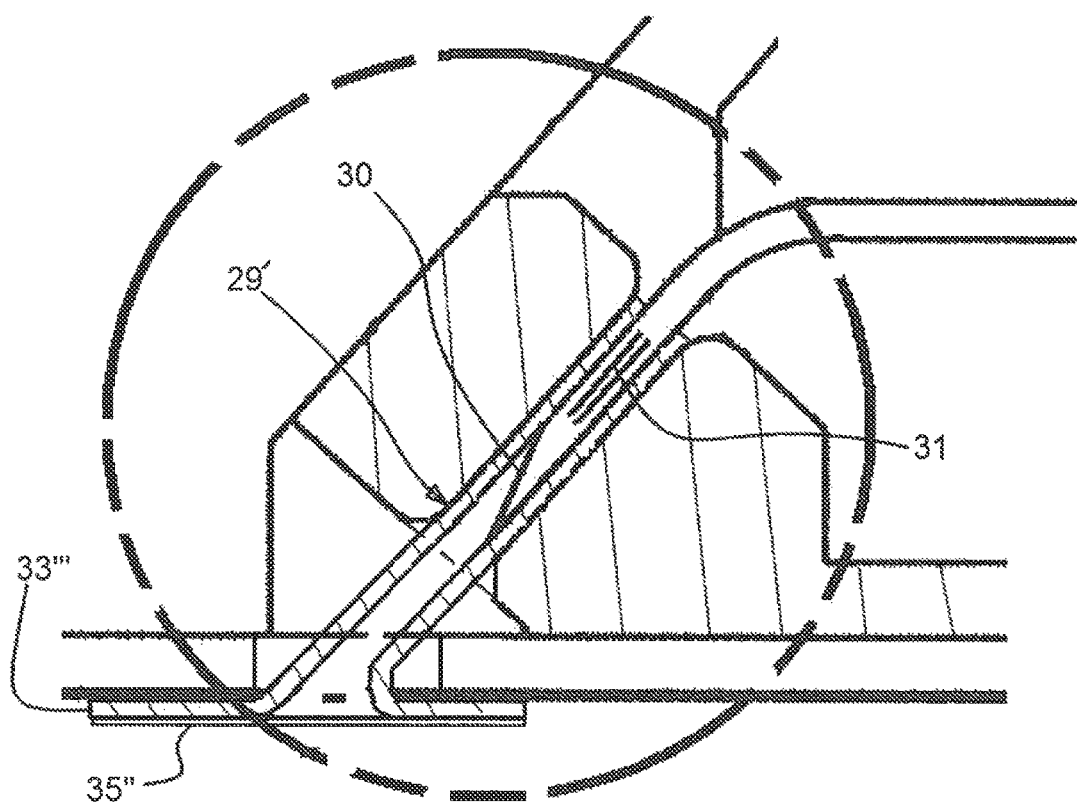
FIG. 7G is a detail view of a further alternate embodiment of the needle assembly disposed as is the embodiment of FIG. 7B.

Referring now to FIG. 7G, a further alternate embodiment of the needle assembly 29' of the invention is shown, which is essentially identical to the embodiments shown in FIGS. 3A and 3B, except that the flange 33" is not perpendicular to the needle 30.

Alternatively, the device 300 may be contained in a variety of injection devices, such as those corresponding to FIGS. 1 to 20A of PCT Application No. PCT/US2012/048044, filed 25 Jul. 2012, the contents of which are incorporated herein by reference thereto.

The devices of the invention may advantageously use the reservoir 12 to store and inject the fluid 27 into the needle assembly 29, and so dissolve the dry carrier or active agent 12, 26 and flush the same into the bloodstream of the living organism 14. To this end, a method for injecting a living organism includes several steps. In a first step, an injection device 10 is attached to a living organism. In a second step, the injection device is activated. In a third step, the activation of the injection device causes a fluid 27 to be injected through the needle assembly 29, into a living organism. The injected fluid dissolves or releases active agents in the dry carrier into the bloodstream of the living organism. The needle 30 in then retracted and the device 10 may be removed and the injection site disinfected.

It should be appreciated that the particular implementations shown and described herein are representative of the invention and its best mode and are not intended to limit the scope of the present invention in any way. Furthermore, any connecting lines shown in the various figures contained herein are intended to represent exemplary functional relationships and/or physical couplings between various elements. It should be noted that many alternative or additional physical connections or functional relationships may be present and apparent to someone of ordinary skill in the field.

Moreover, the apparatus, system and/or method contemplates the use, sale and/or distribution of any goods, services or information having similar functionality described herein.

The specification and figures are to be considered in an illustrative manner, rather than a restrictive one and all modifications described herein are intended to be included within the scope of the invention claimed, even if such is not specifically claimed at the filing of the application. Accordingly, the scope of the invention should be determined by the claims appended hereto or later amended or added, and their legal equivalents rather than by merely the examples described above. For instance, steps recited in any method or process claims should be construed as being executable in any order and are not limited to the specific order presented in any claim. Further, the elements and/or components recited in any apparatus claims may be assembled or otherwise operationally configured in a variety of permutations to produce substantially the same result as the present invention. Consequently, the invention is not limited to the specific configuration recited in the claims.

Benefits, other advantages and solutions mentioned herein are not to be construed as necessary, critical, or essential features or components of any or all the claims.

As used herein, the terms "comprises", "comprising", or any variation thereof, are intended to refer to a non-exclusive listing of elements, such that any process, method, article, composition or apparatus of the invention that comprises a list of elements does not include only those elements recited, but may also include other elements described in this specification. The use of the term "consisting" or "consisting of" or "consisting essentially of" is not intended to limit the scope of the invention to the enumerated elements named thereafter, unless otherwise indicated. Other combinations and/or modifications of the above-described elements, materials or structures used in the practice of the present invention may be varied or otherwise adapted by the skilled artisan to other design without departing from the general principles of the invention.

The patents and articles mentioned above are hereby incorporated by reference herein, unless otherwise noted, to the extent that the same are not inconsistent with this disclosure.

Other characteristics and modes of execution of the invention are described in the appended claims.

Further, the invention should be considered as comprising all possible combinations of every feature described in the instant specification, appended claims, and/or drawing figures which may be considered new, inventive and industrially applicable.

Multiple variations and modifications are possible in the embodiments of the invention described here. Although certain illustrative embodiments of the invention have been shown and described here, a wide range of modifications, changes, and substitutions is contemplated in the foregoing disclosure. While the above description contains many specifics, these should not be construed as limitations on the scope of the invention, but rather as exemplifications of one or another preferred embodiment thereof. In some instances, some features of the present invention may be employed without a corresponding use of the other features. Accordingly, it is appropriate that the foregoing description be construed broadly and understood as being given by way of illustration and example only, the spirit and scope of the invention being limited only by the claims which ultimately issue in this application.

What is claimed is:

1. An active agent injecting device for injecting an active agent into a living organism, the injecting device comprising:
   (a) a main housing adapted to be affixed to the skin of a wearer;
   (b) an energy storage device located inside the main housing, the energy storage device biasing an activation mechanism for autonomous injection, the energy storage device being selected from one of the group of devices consisting of a mechanical energy storage device, a pneumatic energy storage device and an electrical energy storage device, the activation mechanism being selected from one of the group of mechanisms consisting of a mechanical activation mechanism, a pneumatically actuated activation mechanism, and an electrically actuated activation mechanism:
   (c) an injection assembly having a needle having two puncturing ends oriented essentially in the same direction so as to be configured to puncture a tissue or membrane when the needle is moved in a single direction and enclosing a dry carrier affixed to an end portion of the needle, the dry carrier comprising an active agent;
   (d) an hermetically sealed reservoir containing a liquid; and
   (e) a trigger mechanism which triggers the injection assembly to release the needle from the housing to inject the end portion of the needle into a subject individual, and to initiate contraction of the reservoir to cause the liquid to flow over the dry carrier thereby providing a fixed dose of liquid.

2. The device of claim 1, wherein the trigger mechanism is controlled by a sensor.

3. The device of claim 1, wherein the trigger mechanism is controlled by a receiver.

4. The device of claim 3, wherein the receiver is a wireless receiver.

5. The device of claim 3, wherein the trigger mechanism is controlled as a function of time.

6. The device of claim 1, further including a second housing for housing a trigger mechanism, the second housing releasably connectable to the main housing.

7. The device of claim 1, wherein the active agent is selected from one of the group of active agents consisting of drugs, vitamins, antivenoms, serums and medications.

8. The device of claim 1, further comprising:
   a. a needle shaft having slits formed therethrough into an internal channel and a fixation structure to which a dry carrier may be attached;
   b. a protective sleeve having a flange formed thereon, the sleeve being in close sliding contact over the needle shaft; and
   c. sealing means to seal the needle assembly against contamination.

9. The device of claim 8, wherein the sealing means is a septum covering an end of the flange.

10. The device of claim 8, wherein the needle shaft is closed at one end to facilitate gripping.

11. The device of claim 8, further including an integral flange adapted to be biased by a retraction mechanism for retracting the needle of the needle assembly out of the skin of a living organism.

12. The device of claim 1, wherein the dry carrier comprising an active agent comprises an active agent selected from one of the group consisting of:
   a. serum albumin,
   b. nanoparticles,
   c. liposome formulations,
   d. PEG conjugation,
   e. combinations of (b) and (c),
   f. combinations of (c) and (d),
   g. combinations of (b) and (d)
   h. combinations of (b), (c) and (d),
   i. lipoproteins,
   j. stabilized nanoparticles, and
   k. carbohydrate carriers.

13. The device of claim 1, wherein the liquid contained within the reservoir is in fluid communication with but remote from the needle.

14. A method of using the active agent injector of claim 1, the method including the steps of:
   a. preparing the injection area;
   b. removing a security seal on the active agent injector;
   c. removing a protective layer from an adhesive pad of the active agent injector;
   d. adhering the active agent injector to the skin of the user;
   e. opening a trigger panel to allow access to the trigger; and
   f. activating the trigger, thereby initiating a process of active agent injection.

15. A process of active agent injection using the active agent injector of claim 1, the process including the steps of:
   a. initializing an actuation system;
   b. priming the active agent injector;
   c. inserting the needle subcutaneously in an injection area;
   d. releasing the active agent;
   e. retracting the needle;
   f. after use, removing the active agent injector; and
   g. sterilizing the injection area.

16. A process of claim 15, wherein the active agent injection is executed automatically by control electronics in the active agent injector.

17. A method of injecting an active agent in a living organism using the device of claim 1, the method including the steps of:
   a. attaching the injection device to the living organism;
   b. activating the injection device, thereby causing the liquid contained in the reservoir to be injected through the needle, into the living organism;
   c. dissolving into the bloodstream of the living organism using the liquid, active agents in the dry carrier;
   d. retracting the needle; and
   e. removing the device and optionally disinfecting the injection site.

* * * * *